(12) United States Patent
Bonano et al.

(10) Patent No.: US 11,191,916 B2
(45) Date of Patent: Dec. 7, 2021

(54) FILTRATION SYSTEM

(71) Applicant: AG Industries LLC, Saint Louis, MO (US)

(72) Inventors: Samantha Bonano, Williamsville, NY (US); Greg Pepe, Lancaster, NY (US)

(73) Assignee: AG Industries LLC, St. Louis, MO (US)

( * ) Notice: Subject to any disclaimer, the term of this patent is extended or adjusted under 35 U.S.C. 154(b) by 422 days.

(21) Appl. No.: 15/851,908

(22) Filed: Dec. 22, 2017

(65) Prior Publication Data

US 2018/0177962 A1  Jun. 28, 2018

Related U.S. Application Data

(60) Provisional application No. 62/438,040, filed on Dec. 22, 2016.

(51) Int. Cl.
*A61M 16/00* (2006.01)
*A61M 16/10* (2006.01)

(52) U.S. Cl.
CPC ...... *A61M 16/024* (2017.08); *A61M 16/0051* (2013.01); *A61M 16/106* (2014.02); *A61M 16/107* (2014.02); *A61M 2205/18* (2013.01); *A61M 2205/273* (2013.01); *A61M 2205/50* (2013.01); *A61M 2205/6018* (2013.01); *A61M 2205/6054* (2013.01); *A61M 2205/6072* (2013.01); *A61M 2205/75* (2013.01); *A61M 2205/7545* (2013.01)

(58) Field of Classification Search
CPC .............. A61M 16/024; A61M 16/106; A61M 16/107; A61M 16/0051; A61M 2205/18; A61M 2205/273; A61M 2205/50; A61M 2205/6018; A61M 2205/6054; A61M 2205/6072; A61M 2205/75; A61M 2205/7545; A62B 7/00; A62B 7/10; A62B 9/00; A62B 18/00; A62B 18/02; A62B 18/025; A62B 18/04; A62B 18/045; A62B 18/06; A62B 18/08; A62B 23/00; A62B 23/02; A62B 23/025; A62B 23/04; A62B 23/06

See application file for complete search history.

(56) References Cited

U.S. PATENT DOCUMENTS 7,761,188 B2  7/2010  Palmerton et al.
8,095,241 B2  1/2012  Palmerton et al.
9,492,690 B2 *  11/2016  Hamerly ................ A62B 9/006
(Continued)

*Primary Examiner* — Tu A Vo
(74) *Attorney, Agent, or Firm* — Harter Secrest & Emery LLP

(57) ABSTRACT

Presented is a method and apparatus for filtering. An exemplary apparatus includes an air flow generator having a fluid intake fluidly connected to a fluid outlet, and a removable filter operably maintained within the air flow generator to filter a flow of fluid between the fluid intake and the fluid outlet, wherein the removable filter includes an electronic tag operable to transmit identifying information of the removable filter. The apparatus further includes an air delivery tube fluidly connected to the fluid outlet, an air delivery element fluidly connected to the air delivery tube, and a processor operable to communicate with the electronic tag to receive the identifying information of the removable filter.

11 Claims, 4 Drawing Sheets

(56) References Cited

U.S. PATENT DOCUMENTS

Figure 1:
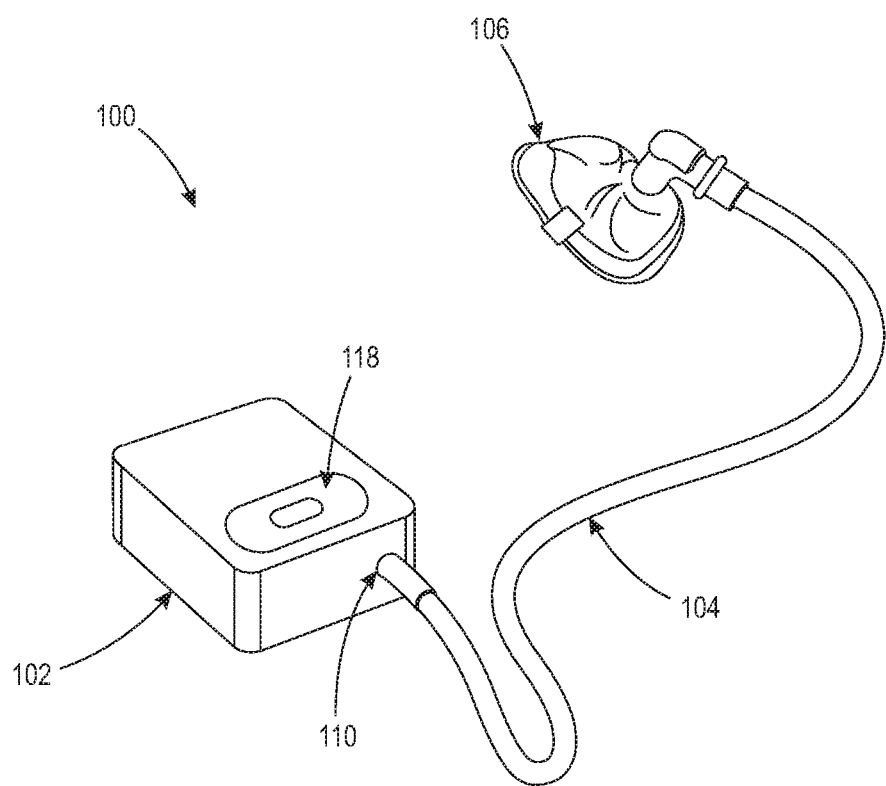

| | | | |
|---|---|---|---|
| 2008/0230450 A1* | 9/2008 | Burbank | A61M 1/1656 |
| | | | 210/92 |
| 2010/0101575 A1* | 4/2010 | Fedorko | A62B 7/10 |
| | | | 128/204.21 |
| 2010/0153023 A1* | 6/2010 | Parham | A62B 9/006 |
| | | | 702/34 |
| 2010/0313892 A1* | 12/2010 | Shigematsu | A62B 18/10 |
| | | | 128/207.12 |
| 2011/0139154 A1* | 6/2011 | Henry | A61M 16/00 |
| | | | 128/204.21 |
| 2013/0239813 A1* | 9/2013 | Rakow | A62B 9/006 |
| | | | 96/108 |
| 2013/0327335 A1* | 12/2013 | Ishikawa | A62B 23/025 |
| | | | 128/205.27 |
| 2015/0165142 A1* | 6/2015 | Tham | A61M 16/08 |
| | | | 128/202.22 |
| 2016/0001102 A1* | 1/2016 | Huh | A62B 7/10 |
| | | | 128/206.17 |
| 2016/0046502 A1* | 2/2016 | Rice | C02F 1/003 |
| | | | 210/85 |
| 2016/0114281 A1* | 4/2016 | Bonano | A61M 1/0001 |
| | | | 96/131 |
| 2016/0151591 A1* | 6/2016 | Le Bars | A61M 16/024 |
| | | | 128/202.22 |
| 2016/0317845 A1* | 11/2016 | Zwolinsky | A61M 16/0875 |
| 2017/0368381 A1* | 12/2017 | Awiszus | A42B 3/225 |

* cited by examiner

FILTRATION SYSTEM

BACKGROUND OF THE INVENTION

Field of the Invention

Embodiments of the present disclosure relates to a method and apparatus for filtration. Embodiments of the present disclosure relate more particularly to a method and apparatus for filtration of air and fluids.

Description of Related Art

Continuous positive airway pressure (CPAP) is a type of positive airway pressure ventilation. CPAP applies air pressure on a continuous basis to keep airways open on a continuous basis in a user able to breathe on their own. A CPAP stent the lungs' alveoli open such that they are able to recruit more of the lung's surface area for ventilation. CPAP devices apply continuous positive airway pressure throughout the breathing cycle. A ventilator on a CPAP device does not cycle on and off during use, and no additional pressure above the continuous pressure provided by the CPAP occurs. The user of the CPAP device must initiate each breath during use. CPAP is generally used by people who have sleep apnea or other breathing issues.

BRIEF SUMMARY OF THE INVENTION

In view of the foregoing, it is an object of the present disclosure to provide an apparatus and method for filtering.

A first exemplary embodiment of the present disclosure provides an apparatus for filtering. The apparatus includes an air flow generator having a fluid intake fluidly connected to a fluid outlet, and a removable filter operably maintained within the air flow generator to filter a flow of fluid between the fluid intake and the fluid outlet, wherein the removable filter comprises an electronic tag operable to transmit identifying information of the removable filter. The apparatus further includes an air delivery tube fluidly connected to the fluid outlet, an air delivery element fluidly connected to the air delivery tube, and a processor operable to communicate with the electronic tag to receive the identifying information of the removable filter.

A second exemplary embodiment of the present disclosure provides a method of filtering. The method includes providing an air flow generator having a fluid intake fluidly connected to a fluid outlet, a removable filter operably maintained within the air flow generator to filter a flow of fluid between the fluid intake and the fluid outlet, wherein the removable filter comprises an electronic tag operable to transmit identifying information of the removable filter, an air delivery tube fluidly connected to the fluid outlet, an air delivery element fluidly connected to the air delivery tube, and a processor operable to communicate with the electronic tag to receive the identifying information of the removable filter. The method further includes determining, by the processor, whether the removable filter is operable with air flow generator based on the identifying information of the removable filter from the electronic tag.

The following will describe embodiments of the present disclosure, but it should be appreciated that the present disclosure is not limited to the described embodiments and various modifications of the disclosure are possible without departing from the basic principle. The scope of the present disclosure is therefore to be determined solely by the appended claims.

BRIEF DESCRIPTION OF THE SEVERAL VIEWS OF THE DRAWING(S)

FIG. 1 presents an exemplary device for filtering suitable for use in practicing exemplary embodiments of this disclosure.

Figure 2:
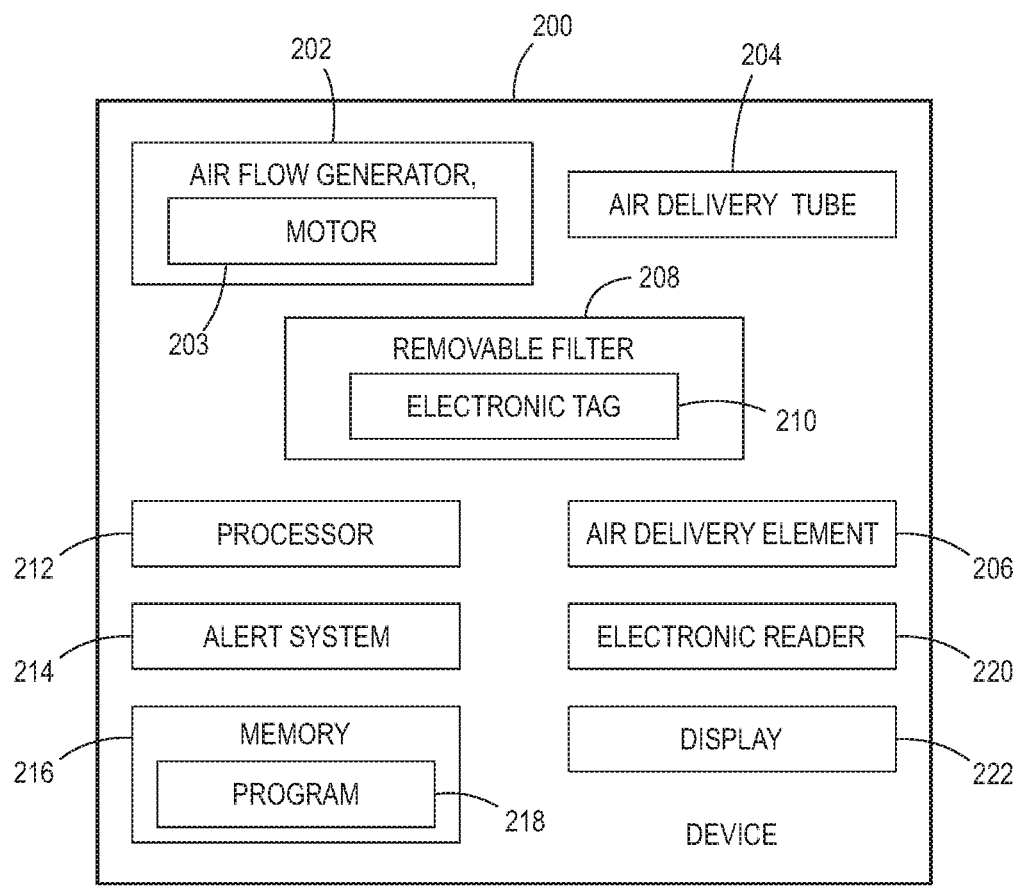

FIG. 2 presents a simplified block diagram of devices suitable for use in practicing exemplary embodiments of this disclosure.

Figure 3:
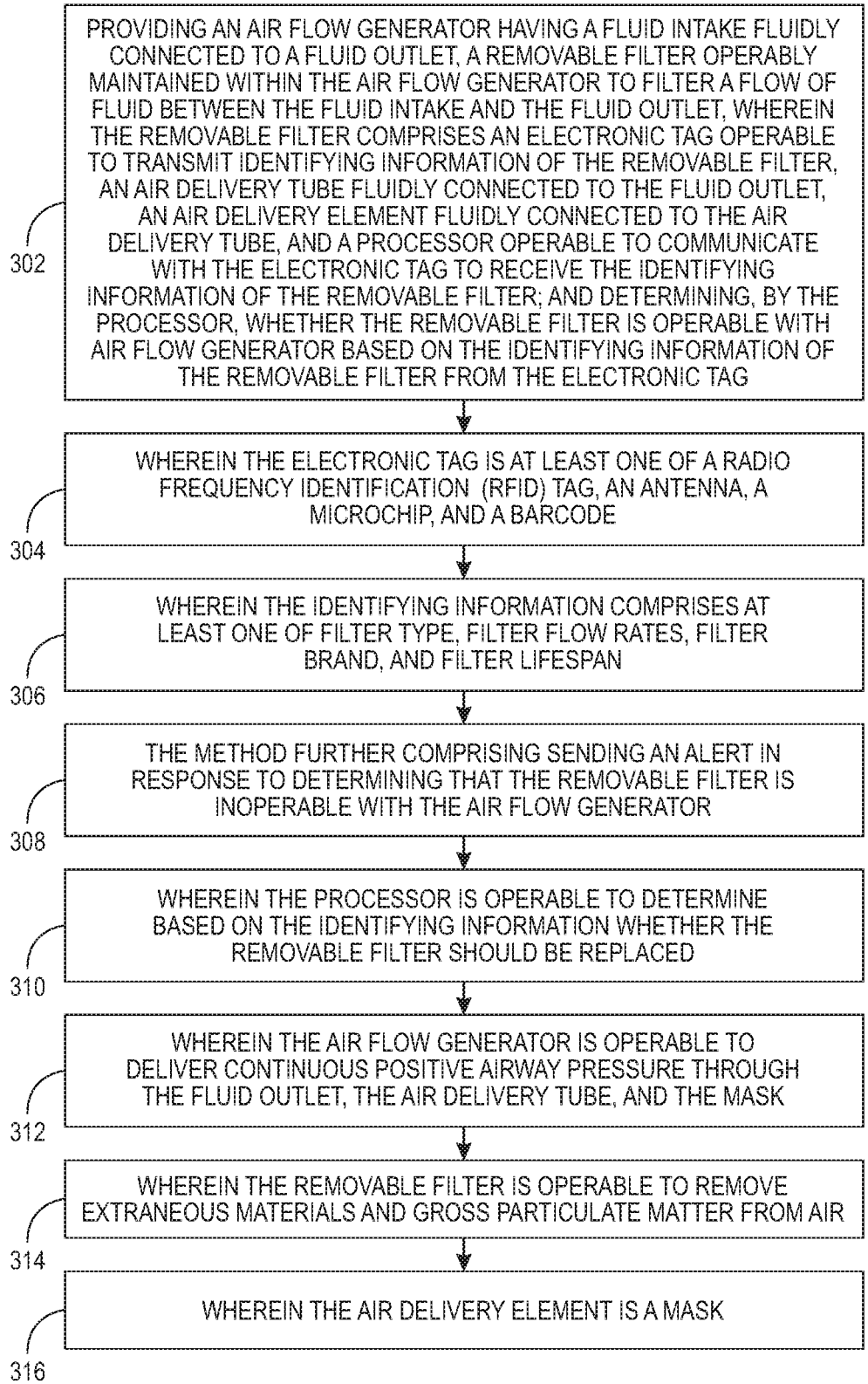

FIG. 3 presents an exemplary logic flow diagram in accordance with a method and apparatus for performing exemplary embodiments of this disclosure.

Figure 4:
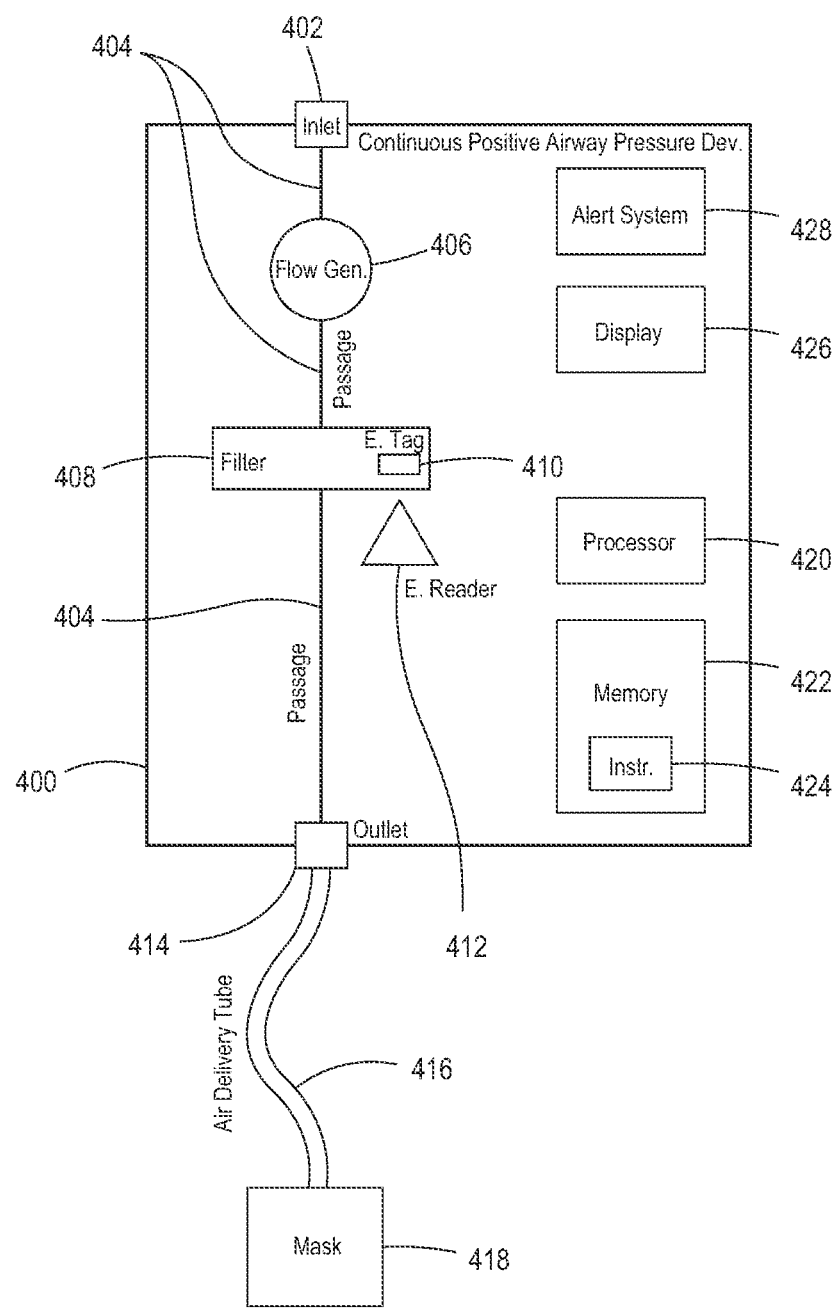

FIG. 4 presents a schematic of an exemplary device for filtering suitable for use in practicing exemplary embodiments of this disclosure.

DETAILED DESCRIPTION OF THE INVENTION

Embodiments of the present disclosure provide an air flow generator (e.g., a continuous positive airway pressure device) having a fluid intake and a fluid outlet. The air flow generator operable to produce a flow of fluid (e.g., air) from the fluid intake out the fluid outlet to an air delivery tube fluidly connected to the fluid outlet. The air delivery tube is operable to receive the flow of fluid and direct it to an air delivery element (e.g., a mask) at which point the user will be able to receive continuous positive airway pressure from the flow of fluid. The air flow generator is operable to maintain a filter operable to filter the flow of fluid between the fluid intake and the fluid outlet. The filter includes an electronic tag (e.g., a radio frequency identification (RFID), an antenna, a microchip, or a barcode) that is operable to maintain identifying information about the filter. The electronic tag is operable to communicate the identifying information about the filter to a processor. The processor may be maintained within the housing of the air flow generator. The processor is operable to determine (based on the identifying information) whether the filter is the appropriate filter for use with the air flow generator. For example, the processor is operable to determine based on the filter type, filter flow rates, filter brand, and/or filter lifespan whether the filter should be replaced. Accordingly, embodiments of the present disclosure provide a CPAP device with a filter that operably notifies the user whether the filter should be replaced.

Referring to FIG. 1, shown is an exemplary device for performing exemplary embodiments of the present disclosure. Shown in FIG. 1 is device 100 having an air flow generator 102, an air delivery tube 104 and a mask 106. Air flow generator 102 includes a fluid intake 108 and a fluid outlet 110. Air flow generator 102 is operable to produce a flow of fluid by pulling air or other fluid through the fluid intake 108 and expelling the flow of fluid or air out of the fluid outlet 110. It should be understood that the flow of fluid may be comprised of liquids, gases, and/or solids. Embodiments of air flow generator 102 include a motor or other similar device operable to produce a flow of fluid.

Air delivery tube 104 is fluidly connected to the fluid outlet 110 to receive the flow of fluid. Air delivery tube 104 is fluidly connected to mask 106 such that air flow generator 102, air delivery tube 104, and mask 106 are operable to provide a user with continuous positive airway pressure.

Air flow generator 102 operably maintains at least one filter 112. Filter 112 is operable to filter extraneous materials, gross particulate matter and other unwanted particles from the flow of fluid flowing between the fluid intake 108 and the fluid outlet 110. Some of the extraneous materials can include visible or microscopic particles, organic, or inorganic matter. Filter 112 is removable and replaceable from air flow generator 102. Embodiments of filter 112 include an electronic tag 114. Examples of electronic tag 114 include a radio frequency identification (RFID) tag, an antenna, a microchip, and/or a barcode. Electronic tag 114 are operable to maintain identifying information about filter 112. Examples of identifying information include filter type, filter flow rates, filter brand, and filter lifespan.

Device 100 also includes at least one processor 116. Processor 116 is operable to communicate with electronic tag 114 and to determine based on the identifying information on the electronic tag 114 whether filter 112 should be replaced. Some embodiments of device 100 also include at least one alert system 118. The alert system 118 can include any one or combination of signals (e.g., light, vibration, audible sound, etc.) that notifies the user that the filter 112 should be changed. Embodiments of alert system 118 are operably to controlled by or communicate with processor 116 and can send an alert based on whether the processor 116 determines that the filter 112 should be replaced.

Reference is now made to FIG. 2, which depicts a simplified block diagram of devices suitable for use in practicing exemplary embodiments of this disclosure. Shown in FIG. 2 is device 200 having an air flow generator 202 with a motor 203 for producing a flow of fluid or air. Device 200 also includes an air delivery tube 204 for receiving and transmitting the flow of fluid to air delivery element 206 (e.g., air delivery tube and mask). Device 200 includes a removable filter 208 having an electronic tag 210, which maintains identifying information about filter 208.

Device 200 further includes a processor 212 operable to communicate with the electronic tag 210 and to receive the identifying information. Some embodiments of device 200 include an electronic reader 220 operable to obtain the identifying information from electronic tag 210 and communicate the obtained identifying information to processor 212. In one embodiment electronic reader 220 is an antenna arranged such that it is operable to communicate with electronic tag 210. Processor 212 is also operable to communicate with alert system 214 for alerting a user to replace or change removable filter 208. In some embodiments device 200 also includes a memory 216 operable to communicate with processor 212 such that processor 212 can access program 218 stored on memory 216. Program 218, when accessed or run on processor 212, can instruct processor 212 and device 200 to operate or perform operations as described herein.

Processor 212 with memory 216 and program 218 is also operable to calculate and display with display 222 the remaining life of removable filter 208. Embodiments provide that the established or rated filter life of removable filter 208 can be written on to electronic tag 210, along with such information as filter type or name, manufacturer, and manufacturing lot number. When a new removable filter 208 is inserted into device 200, processor (with electronic reader 220) reads and stores the identifying information in memory 216. Some examples of information that can be displayed on display 222 include filter life, which may be based on a particular air flow generator 202 speed or intake flow rate which is a function of motor 203 speed.

Referring to FIG. 3, illustrated is a logic flow diagram in accordance with a method and apparatus for performing exemplary embodiments of this disclosure. Block 302 presents providing an air flow generator having a fluid intake fluidly connected to a fluid outlet, a removable filter operably maintained within the air flow generator to filter a flow of fluid between the fluid intake and the fluid outlet, wherein the removable filter comprises an electronic tag operable to transmit identifying information of the removable filter, an air delivery tube fluidly connected to the fluid outlet, an air delivery element fluidly connected to the air delivery tube, and a processor operable to communicate with the electronic tag to receive the identifying information of the removable filter; and determining, by the processor, whether the removable filter is operable with air flow generator based on the identifying information of the removable filter from the electronic tag. Following block 302, block 304 specifies wherein the electronic tag is at least one of a radio frequency identification (RFID) tag, an antenna, a microchip, and a barcode.

Some of the non-limiting implementations detailed above are also summarized at FIG. 3 following block 304. Block 306 presents wherein the identifying information comprises at least one of filter type, filter flow rates, filter brand, and filter lifespan. Then block 308 relates the method further comprising sending an alert in response to determining that the removable filter is inoperable with the air flow generator. Block 310 states wherein the processor is operable to determine based on the identifying information whether the removable filter should be replaced. Next block 312 indicates wherein the air flow generator is operable to deliver continuous positive airway pressure through the fluid outlet, the air delivery tube, and the mask.

Block 314 states wherein the removable filter is operable to remove extraneous materials and gross particulate matter from air. Lastly, block 316 specifies wherein the air delivery element is a mask.

The logic diagram of FIG. 3 may be considered to illustrate the operation of a method, a result of execution of computer program instructions stored in a computer-readable medium, or the operation of an apparatus. The logic diagram of FIG. 3 may also be considered a specific manner in which components of a device are configured to operate, whether such a device is a CPAP device or one or more components thereof.

Referring to FIG. 4, shown is yet another exemplary continuous positive airway pressure device 400 suitable for performing exemplary embodiments of the present disclosure. Shown in FIG. 4 is device 400 having a fluid inlet 402 that is fluidly connected to air flow generator 406. Air flow generator 406 is fluidly connected to filter 408, fluid outlet 414, air delivery tube 416 and mask 418. Filter 408 includes an electronic tag 410, which can be read by electronic reader 412. Embodiments of filter 408 provide that it can be removed and replaced from device 400 as desired by a user. Embodiments of filter 408 are operable to remove extraneous materials and gross particulate matter from air or fluid passing through passage 404. Air flow generator 406 is operable to produce a flow of fluid by pulling air or other fluid through fluid inlet 402 and expelling it through filter 408 and out fluid outlet 414, air delivery tube 416 and mask 418.

Electronic tag 410 is operable to communicate with processor 420. Embodiments of electronic tag 410 include a radio frequency identification (RFID) tag, an antenna, a microchip and/or a barcode. Electronic tag 410 is operable to transmit to the electronic reader 412 identifying information regarding filter 408. Exemplary identifying information include filter type, filter flow rates, filter brand, and filter lifespan. Processor 420 is operable to communicate with and operate memory 422 having computer program instructions 424, display 426 (which can include a user interface for operating device 400), and alert system 428. Fluid inlet 402, air flow generator 406, filter 408 and fluid outlet 414 are fluidly connected through passage 404, which is operable to allow a flow of fluid through device 400. Processor 420 is further operable to determine based on the identifying information from electronic tag 410 whether filter 408 is compatible with device 400. Compatibility can include whether filter 408 is operable to filter out the correct amount of gross particulate matter from fluid that passes through filter 408. Compatibility can also include size and brand of filter 408. Processor 420 is also operable to determine based on the identifying information from electronic tag 410 whether filter 408 should be replaced due to the length of time filter 408 has been in use or due to build up on gross particulate matter in filter 408. Processor 420 is operable to control display 426 and/or alert system 428 to signal and/or display to a user that filter 408 should be replaced, that filter 408 is compatible or incompatible with device 400, the filter type, filter flow rate, filter brand and filter lifespan of filter 408. Embodiments of device 400 are operable to deliver continuous positive airway pressure to a user wearing mask 418 through fluid outlet 414, air delivery tube 416 and mask 418.

Various embodiments of the computer-readable medium include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. Various embodiments of the processor include but are not limited to general purposed computers, special purpose computers, microprocessors, digital signal processors, and multi-core processors.

This disclosure has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention in indicated by the appended claims, and all changes that come within the meaning and range of equivalents thereof are intended to be embraced therein.

The invention claimed is:

1. An apparatus for filtering, the apparatus comprising:
   (a) an air flow generator having a fluid intake fluidly connected to a fluid outlet;
   (b) a removable filter operably maintained within the air flow generator to filter a flow of fluid between the fluid intake and the fluid outlet, wherein the removable filter comprises an electronic tag operable to transmit identifying information of the removable filter, wherein the identifying information comprises at least a flow rate of the removable filter;
   (c) an air delivery tube fluidly connected to the fluid outlet;
   (d) an air delivery element fluidly connected to the air delivery tube, wherein the air delivery element is a mask;
   (e) a processor operable to communicate with the electronic tag to receive the identifying information of the removable filter, wherein the processor is operable to determine whether the removable filter is compatible with the air flow generator as a function of the flow rate of the removable filter; and
   (f) an alert system comprising at least one of a light alarm or an audible alarm, the alert system operable to signal a user that the removable filter is inoperable with the air flow generator.

2. The apparatus according to claim 1, wherein the electronic tag is at least one of a radio frequency identification (RFID) tag, an antenna, a microchip, and a barcode.

3. The apparatus according to claim 1, wherein the processor is operable to determine based on the identifying information whether the removable filter should be replaced.

4. The apparatus according to claim 1, wherein the air flow generator is operable to deliver continuous positive airway pressure through the fluid outlet, the air delivery tube, and the air delivery element.

5. The apparatus according to claim 1, wherein the removable filter is operable to remove extraneous materials and gross particulate matter from air.

6. The apparatus according to claim 1, wherein the processor is operable to determine a lifespan of the removable filter as a function of an intake flow rate of the air flow generator.

7. A method of filtering, the method comprising:
   (a) providing an air flow generator having a fluid intake fluidly connected to a fluid outlet, a removable filter operably maintained within the air flow generator to filter a flow of fluid between the fluid intake and the fluid outlet, wherein the removable filter comprises an electronic tag operable to transmit identifying information of the removable filter, an air delivery tube fluidly connected to the fluid outlet, an air delivery element fluidly connected to the air delivery tube, and a processor operable to communicate with the electronic tag to receive the identifying information of the removable filter, wherein the air delivery element is a mask, and wherein the identifying information comprises at least a flow rate of the removable filter;
   (b) determining, by the processor, whether the removable filter is compatible with the air flow generator based on at least the flow rate of the removable filter; and
   (c) sending an alert, by an alert system comprising at least one of a light alarm or an audible alarm, in response to determining that the removable filter is inoperable with the air flow generator.

8. The method according to claim 7, wherein the electronic tag is at least one of a radio frequency identification (RFID) tag, an antenna, a microchip, and a barcode.

9. The method according to claim 7, wherein the processor is operable to determine based on the identifying information whether the removable filter should be replaced.

10. The method according to claim 7, wherein the air flow generator is operable to deliver continuous positive airway pressure through the fluid outlet, the air delivery tube, and the mask.

11. The method according to claim 7, wherein the removable filter is operable to remove extraneous materials and gross particulate matter from air.

* * * * *